United States Patent [19]

Schick

[11] 4,272,483

[45] Jun. 9, 1981

[54] SOLUTION HANDLING APPARATUS AND METHOD

[75] Inventor: Karl G. Schick, Whitefish Bay, Wis.

[73] Assignee: Fiatron Systems, Inc., Milwaukee, Wis.

[21] Appl. No.: 57,369

[22] Filed: Jul. 13, 1979

[51] Int. Cl.³ .................... G01N 21/00; G01N 31/00
[52] U.S. Cl. .................................... 422/67; 422/82; 422/64; 73/863.71
[58] Field of Search .................. 422/70, 81, 82, 89, 422/64, 67, 68, 76, 116; 23/230 A, 232 C, 230 R; 73/422 GC, 423 A; 141/130

[56] References Cited

U.S. PATENT DOCUMENTS

| | | | |
|---|---|---|---|
| 2,833,151 | 5/1958 | Harvey | 73/422 GC |
| 3,065,060 | 11/1962 | Roehrig et al. | 422/89 |
| 3,285,701 | 11/1966 | Robertson | 422/89 |
| 3,479,880 | 11/1969 | Mutter et al. | 73/422 |
| 3,649,203 | 3/1972 | Schneider | 422/81 |
| 3,690,833 | 9/1972 | Ferrari | 23/230 R |
| 3,858,450 | 1/1975 | Jones | 73/423 A |
| 3,881,872 | 5/1975 | Naono | 23/230 R |
| 4,013,413 | 3/1977 | Stewart et al. | 23/230 R |
| 4,022,575 | 5/1977 | Hansen et al. | 23/230 R |
| 4,102,648 | 7/1978 | Hartmann et al. | 422/54 |
| 4,108,602 | 8/1978 | Hanson et al. | 422/81 |
| 4,148,610 | 4/1979 | Miller et al. | 422/81 |

FOREIGN PATENT DOCUMENTS 2806157 10/1978 Fed. Rep. of Germany ............. 422/81

Primary Examiner—William F. Smith
Assistant Examiner—Chris Konkol
Attorney, Agent, or Firm—McDougall, Hersh & Scott

[57] ABSTRACT

A solution handling device is disclosed which employs flow injection to maximize sampling rate with minimum reagent volume required per sample. The device employs two sample loops and a pair of solenoid actuated four-way valves for controlling flow through the loops. While a first loop receives electrolyte, a second loop, having previously received a sample, is channeled to an analyzer for a specified purpose. Subsequently, the valve operation is reversed so that operation is substantially continuous.

10 Claims, 6 Drawing Figures

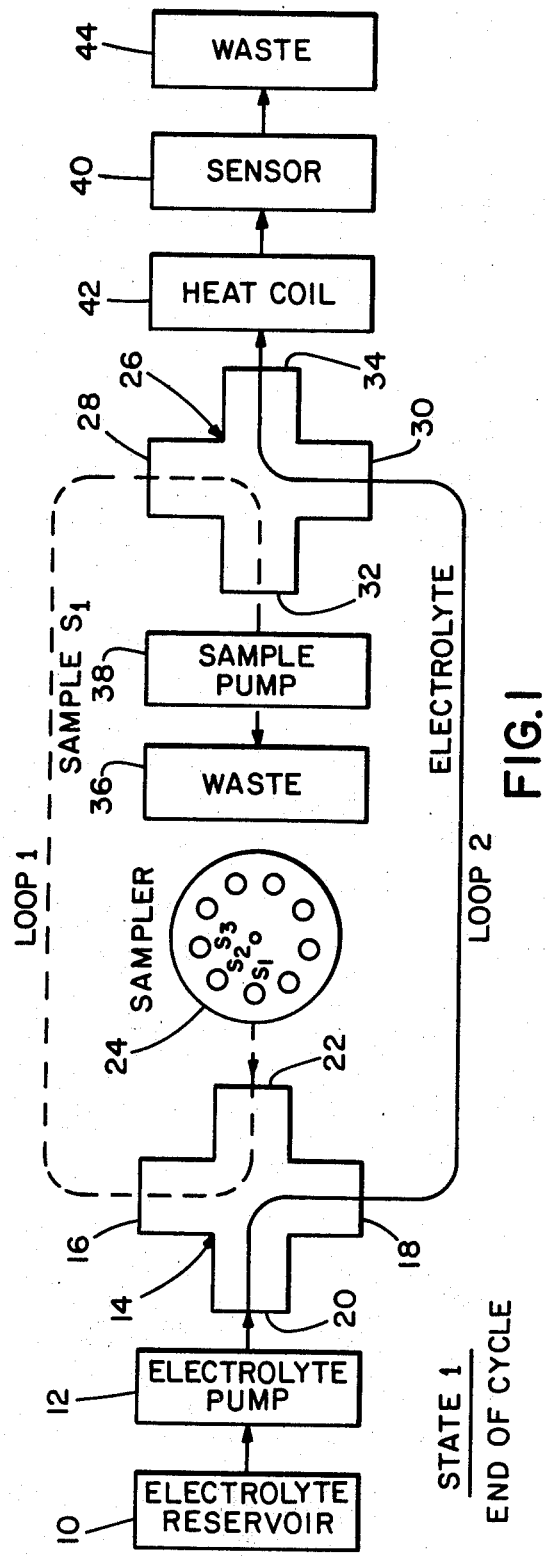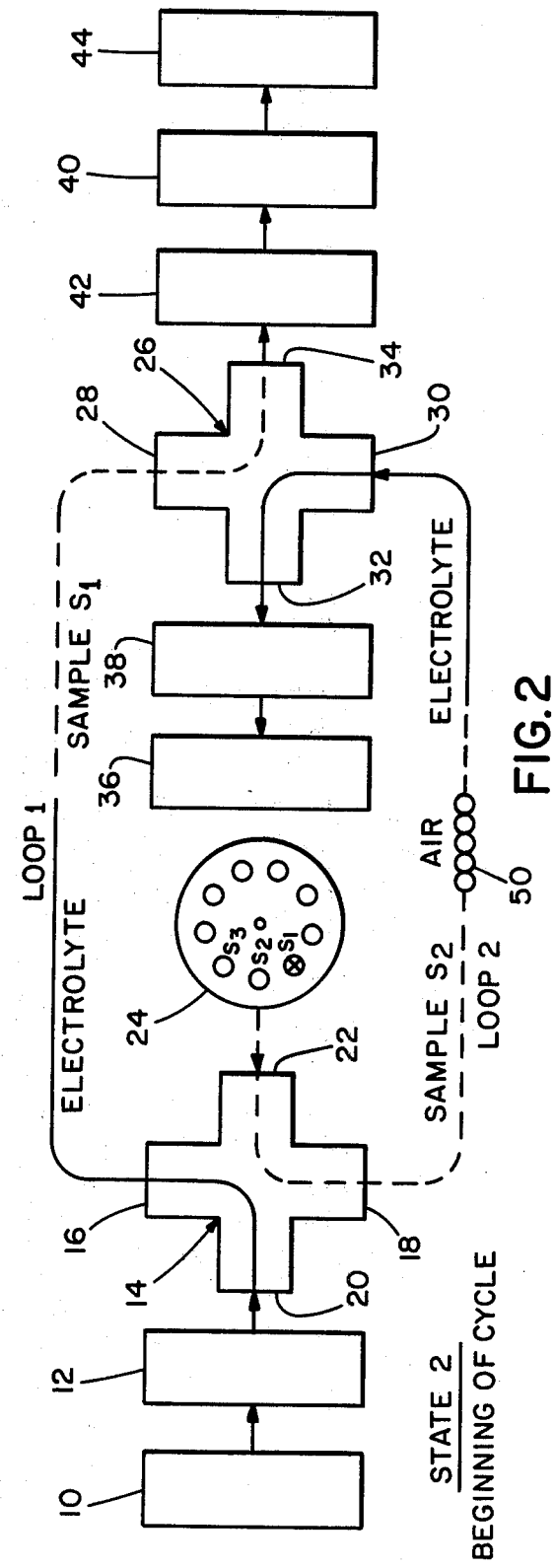

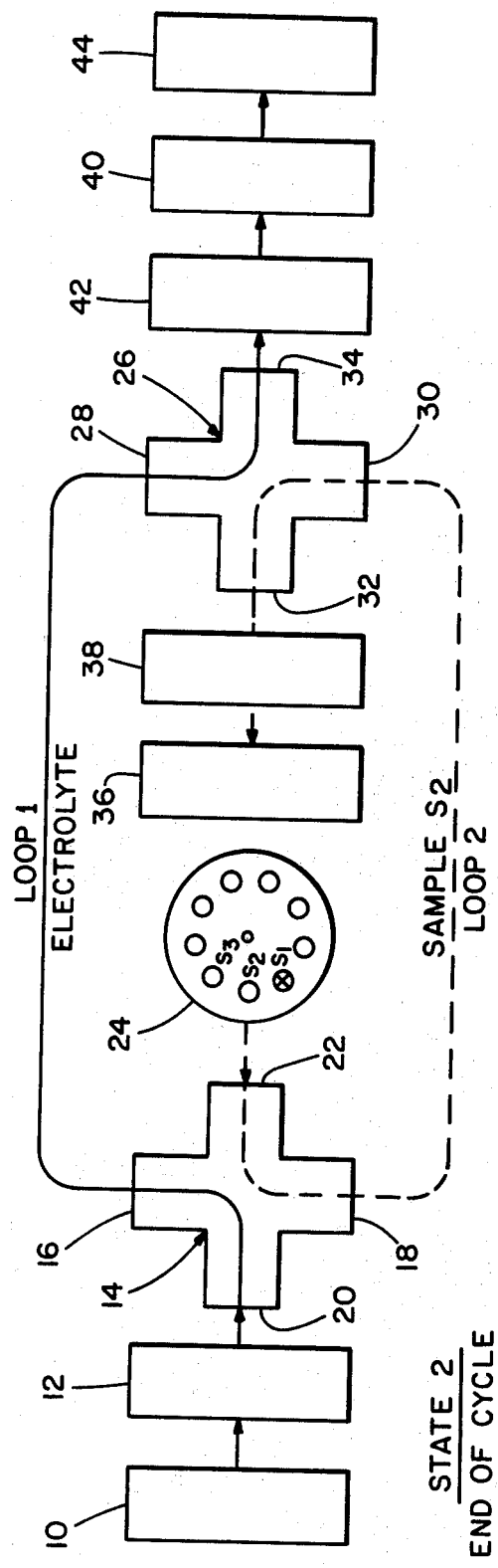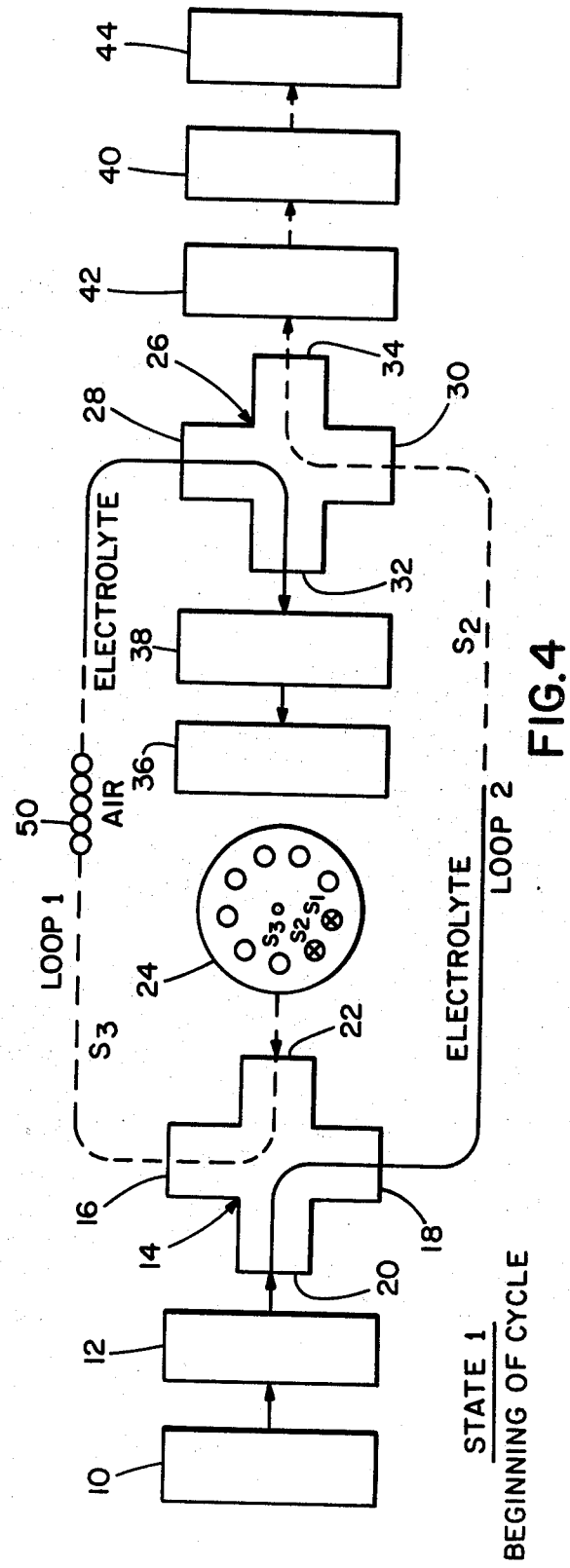

SOLUTION HANDLING APPARATUS AND METHOD

BACKGROUND OF THE INVENTION

The ever increasing demand for greater analytical productivity, i.e. in the clinical, agricultural and pharmaceutical industries, has led to the development of a variety of automated analytical instruments. The developments in this field have been stimulated by the many advantages gained through automation, e.g., increased precision, decreased cost per assay, as well as the increased reliability of automated equipment. Automated chemical analyzers can be divided into two main groups: batch analyzers and continuous flow analyzers.

In the batch analyzer, each sample is placed in its individual container within which it remains during the course of the analytical procedure. The containers proceed through the instrument on a moving belt, where reagents are added at predetermined points and times. Finally, when the treated sample reaches the detector unit (spectrophotometer, flame photometer, etc.), it is pumped into a flow through cell where the actual measuring procedure is carried out. Each sample is evaluated separately in the analyzer, i.e., it operates discontinuously. The disadvantage of batch analyzers is that they contain complex moving parts which eventually become worn during use, and there are problems associated with washing and/or discarding the containers after use. Also these instruments are less versatile than continuous flow analyzers.

In prior art continuous flow analyzers, the samples are successively aspirated from their individual containers into a tube through which the samples move until the entire analysis is completed. In this way, the samples which successively follow each other become part of a continuously moving stream into which, at predetermined points and times, reagents are continuously added at fixed flow rates. The processed stream finally reaches a flow through cell of a spectrophotometer (or other measuring device) where the signal is quantitated. The greatest advantage of continuous flow analyzers is their simplicity and their versatility which allows an easy programming of the flowing stream (which, for instance, might be split for multiple analysis). The disadvantage of the continuous flow concept is primarily the potential possibility of carry-over.

There are two types of continuous flow analyzers, the air segmented flow analyzer and the flow injection analyzer. The former separates successive samples in a continuous tube by means of air bubbles. Flow injection analysis, a relatively new method of continuous flow analysis, is based on the formation and exploitation of concentration profiles of samples injected into an unsegmented carrier stream. This procedure allows for considerably greater sampling rates than those typically found in air segmented flow analysis.

The introduction of an air bubble into a flowing stream made the continuous flow analysis practical. The role of the air bubble is simply to segment the flowing stream and thus minimize carry-over effects. Thus, in one commercially available system in which this principle is used, the continuously flowing stream is regularly and frequently segmented by air bubbles which effectively sweep the tubes, thereby allowing the sampling rate to increase up to about 100 samples per hour. A further increase of the sampling rate is hindered by the necessity of reaching, for each individual sample, a "steady state" signal level. Consequently, long sampling times are required in order to achieve the necessary precision of analysis, thus limiting the output of the continuous analyzer. Sampling rates in excess of 100 samples per hour result in carry-over effects and less precision.

Studies of the kinetic parameters which characterize continuous flow systems have established that the attainment of a "steady state" signal level is not required provided that the sample is introduced into the continuously flowing stream over an exact period of time. However, the utilization of such "transient" signals requires a high precision of sampling, which is impossible to achieve in present systems. This is due to the difficulties with precise sampling; irregularities in the pumping action of the peristaltic pump manifested by periodical pulsations of all streams; and the presence of the air bubbles.

The "flow injection analysis" system, a second type of continuous flow analyzer, introduces samples directly into a continuously flowing carrier stream. Unlike the prior art where the sampling tube continuously introduces material (sample—air—wash—air—sample, etc.) which then joins a flowing stream of reagents, the flow injection analysis is based upon discrete injection of a well defined volume of sample into a continuously flowing stream of reagents, which is then carried towards the detector. The reagents, necessary for a particular analysis, can be present in the carrier stream into which the samples are being injected. Additional reagents can be added at positions further down the line on the way to the detector.

Depending on the flow rate of the carrier system, sampling rates in excess of 300 samples per hour are attainable. This very fast sampling rate is possible because flow injection analysis utilizes "transient" signals rather than "steady state" signals which are used in air segmented flow analysis. Furthermore, the volume of reagent needed per analysis is smaller in flow injection analysis than in air segmented flow analysis. Only a small volume of sample is required (0.5 ml or less) with the flow injection analysis procedure which creates well defined, narrow segments of sample, resulting in well pronounced detector signals.

It is accordingly an object of the present invention to provide a dual channel solution handling apparatus for flow injection analysis and liquid chromatography.

It is another object of the present invention to provide a dual channel solution handling apparatus which does not require any solution or sample bypassing.

A further object of the invention is to provide a device of the type described which does not require a wash or cleaning cycle between samples.

Another object of the invention is to provide a device of the type described which does not require the use of air bubbles to separate samples.

Another object of the invention is to provide a device of the type described in which background electrolyte and samples are simultaneously injected into opposite loops permitting a high sampling rate.

A further object of the invention is to provide a device of the type described which is highly efficient in terms of maximizing sampling rate while minimizing reagent volume needed per sample as measured by the system efficiency index (SEI).

Yet another object of the invention is to provide a system which can be digitally controlled for optimizing system operation.

Other objects and advantages of the invention will be apparent from the remaining portion of the specification.

BRIEF DESCRIPTION OF THE DRAWINGS

FIGS. 1 through 4 are state diagrams schematically indicating the apparatus according to the present invention at various times during the two operating states.

DETAILED DESCRIPTION

Figure 5:
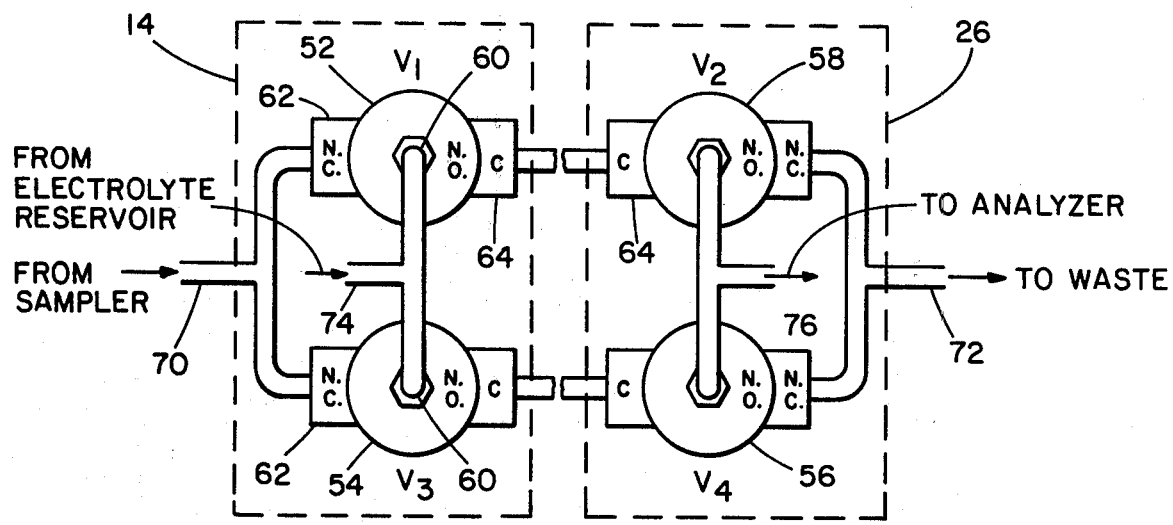
FIG. 5 is a plan view of a valve arrangement suitable for use in the present invention.

In general, the device is intended for any application in which a portion of one solution or solution stream is to be injected into a second solution or solution stream. The invention is intended for use in low and medium pressure liquid chromatography. This device will make it possible to automatically introduce new samples onto a liquid chromatography column.

The invention is also intended for use in industrial and clinical instrumentation. The device can be used in conjunction with any flow through detector capable of handling small volumes of solutions. Commercially available fluorometric, colorometric, potentiometric, amperometric or conductometric flow through devices can be employed.

Referring to FIGS. 1 through 4, a dual channel sample injection device is disclosed according to the invention. Background electrolyte is supplied from a reservoir 10 by operation of an electrolyte pump 12 connected to a four-way solenoid valve indicated at 14. The four-way valve, described in connection with FIG. 5, may be a unitary type preferably of a subminiature construction. Alternatively, valve 14 can be constructed from two subminiature three-way solenoid valves as described in connection with FIG. 5. As will be apparent to those skilled in the art, the electrolyte from the reservoir 10 enters valve 14 and can be directed through a first loop designated loop 1 or a second loop designated loop 2 through valve outlets 16 and 18, respectively. The inputs to valve 14 are at inlets 20 and 22 where electrolyte and samples enter the valve.

Samples are provided from a commercially available sampler 24. Loops 1 and 2 are fluid carrying tubes formed of inert material and carry the electrolyte and samples to a second four-way valve 26 having inlets 28 and 30 and outlets 32 and 34. Outlet 32 leads to a waste receptacle 36 via a sample pump 38. Outlet 34, in the case where the device is used as a flow injection analyzer, is connected to a sensor 40 via a heating coil 42. From the sensor the samples pass into a second waste receptacle 44.

The working principle of this device, as will be explained, is the provision of a dual channel solution handling and sample injecting device consisting of two pumps, preferably peristaltic. When used as a flow injection analyzer, a sensor (spectrophotometric, electrochemical, etc.) together with a read out device and various solution storage containers are used in conjunction with the basic elements illustrated. When the device is used in conjunction with low pressure liquid chromotography, the heating coil 42 is replaced by a liquid chromatography column.

The dual channels of the device, as represented by loop 1 and loop 2, are capable of simultaneously carrying two fluid streams without permitting any intermixing of the fluids. Similarly, the valves 14 and 26 are capable of simultaneously transmitting fluid streams into loops 1 and 2 without permitting any mixing of the streams in the valve. The valves are selectively operable so that the electrolyte input to valve 14 at inlet 20 can be directed to loop 1 or loop 2 as desired via outlets 16 or 18. A similar statement is true with respect to sample inlet 22. Valve 26 can receive the fluid from loop 1 via an inlet 28 and pass it to either of outlets 32 and 34. A similar statement is true of fluid from loop 2 via inlet 30.

In operation valves 14 and 26 are operated simultaneously. When the solenoids for valves 14 and 26 change state, the sample streams are re-directed through different outlets than in their previous state. This switching action is the means by which a sample is injected into the electrolyte and simultaneously electrolyte is injected into a sample stream. The background electrolyte stream which has a small portion of the sample injected therein is utilized analytically, i.e., the sample plug is quantitized as it passes through the sensor 40. Simultaneously, the sample stream having the background electrolyte injected therein is discarded via the waste container 36.

The switching action of the valves 14 and 26 is controlled by the solenoid driver circuit illustrated and described in connection with FIG. 6. Operation of the flow injection device according to the present invention will be described with reference to FIGS. 1 to 4. FIG. 1 illustrates a first state at the end of a cycle. In FIG. 1 a sample S1 is present in and substantially fills loop 1 while background electrolyte is present in and substantially fills loop 2. In this state valve 14 has inlet 20 connected to outlet 18 and inlet 22 connected to outlet 16. Sample S1 having been injected into loop 1 during the beginning of the cycle (illustrated in FIG. 4), the analysis has not yet taken place. The sample S1 in loop 1 is initially discharged through outlet 32 into the waste receptacle 36. Loop 2 is filled with background electrolyte in preparation for the subsequent injection of a sample S2 thereto.

Referring to FIG. 2, state 2 is illustrated at the beginning of the cycle. State 2 is initiated by switching valves 14 and 26 so that inlet 20 is connected to outlet 16; inlet 22 is connected to outlet 18 with similar and simultaneous changes in valve 26 as illustrated. When this switching occurs sample S2 is injected into loop 2 along with air bubbles indicated at 50, the air bubbles are being introduced into the system when the sampler 24 changes from sample S1 to sample S2. Simultaneously, background electrolyte is provided to loop 1 trailing sample S1.

Sample S1 is now provided via inlet 28, outlet 34 and heating coil 42 to the sensor 40 for analysis. Summarizing, during the first portion of state 2 sample S1 in loop 1 passes the sensor while sample S2 is injected into loop 2 previously filled with electrolyte.

Referring to FIG. 3, the second portion of state 2 is illustrated. Note that valves 14 and 26 remain in the same position as indicated in FIG. 2. In FIG. 3 loop 1 is filled entirely with electrolyte since all of sample S1 has passed through valve 26. Similarly, loop 2 is filled solely with sample S2 since the electrolyte and air bubbles 50 have passed through the pump 38 to the waste receptacle 36. The device is now ready to switch back to state 1.

Referring to FIG. 4, the first portion of state 1 is illustrated. Valves 14 and 26 have returned to their initial positions indicated in FIG. 1. Sample S3 is therefore injected into loop 1 while electrolyte is injected into loop 2. The remaining electrolyte in loop 1 along with air bubbles 50 are destined for waste receptacle 36 while sample S2 passes through the sensor 40 for analysis. The operation continues as illustrated in FIG. 1. The operation illustrated in FIGS. 1 through 4 continues for each sample in sampler 24.

From the foregoing operating description it will be seen that each loop is filled with background electrolyte, subsequently that loop has a sample injected therein. This sample is then provided to the sensor for analysis after which the loop is refilled with electrolyte. This activity takes place in an alternating sequence. Thus, when loop 1 has electrolyte injected therein, loop 2 is injected with a sample and vice versa. Similarly, while loop 1 is being analyzed loop 2 is being prepared for analysis.

Referring now to FIG. 5, a solenoid operated valve arrangement suitable for use in the present invention is illustrated. In the illustrated embodiment the four-way valve arrangement is constructed from four subminiature three-way solenoid valves 52, 54, 56 and 58 interconnected in the manner illustrated. Valves suitable for use in the invention are manufactured by Angar Scientific Controls, Technetics Division of Brunswick Corporation and, for example, Model 336 or 008 may be used.

Valves 52 and 58 are operated in unison as are valves 54 and 56. Thus, valves 52 and 58 will be energized while valves 54 and 56 are de-energized and vice versa. Valves 52 and 54 correspond to the four-way valve 14 illustrated in FIGS. 1 through 4 while valves 56 and 58 correspond to the four-way valve 26. Portions of loop 1 and loop 2 are indicated between the two valve assemblies. Each of the four valves includes a normally open (NO) passage 60, a normally closed (NC) passage 62 and a common passage (C) 64. The common passages 64 of valves 52 and 58 are connected by conduit to form loop 1 while the common passages of valves 54 and 56 are connected to form a loop 2.

When valves 52 and 58 are energized, the inlet 70, connected to the NC inputs valves 52 and 54 is connected through valve 52 to common output 64. Similarly, the common input of valve 58 is connected to outlet 72. Since valves 54 and 56 are not energized, the inlet 74 is connected through NO inlet 60 of valve 54 to valve 56 and outlet 76. When the state of the valves is reversed, inlet 70 will communicate with outlet 72 via valves 54 and 56. The converse is true with respect to inlet 74 and outlet 76. This operation is precisely that required for the four-way valves 14 and 26. With respect to each individual valve, either the normally closed or normally open passage is communicated with the common passage as a function of its control solenoid.

Figure 6:
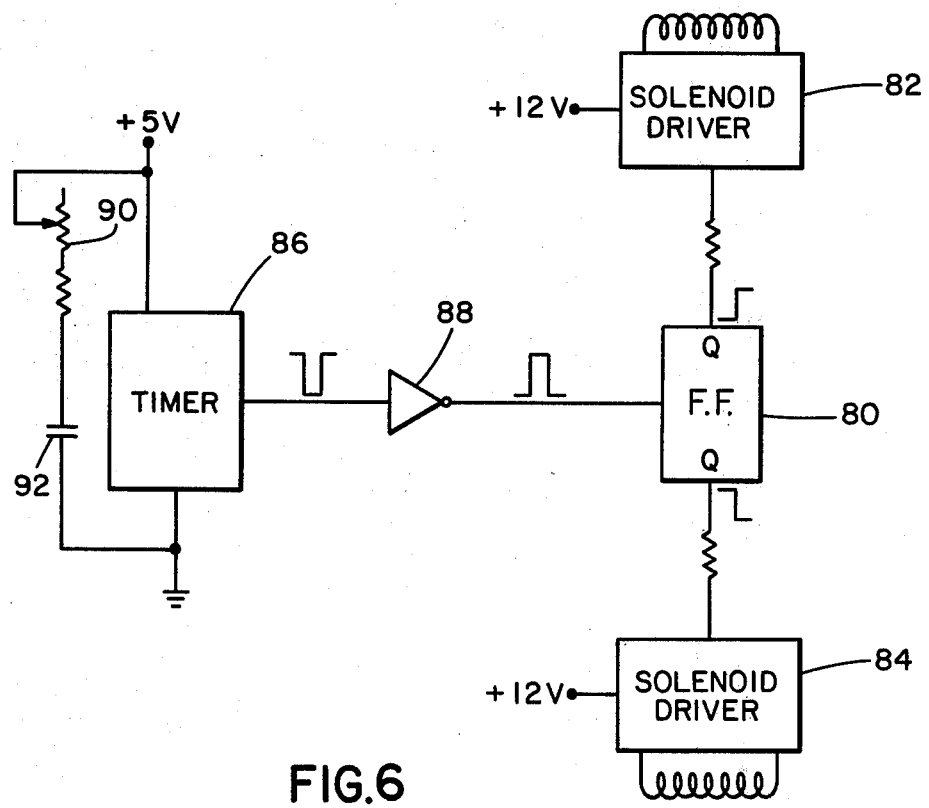
FIG. 6 is a schematic circuit diagram of a control circuit suitable for use in the present invention.

Referring now to FIG. 6, a schematic diagram of the control circuit according to the invention is illustrated. Switching action of the valves is accomplished by toggling a flip-flop 80 and connecting a first solenoid driver circuit 82 to the Q output and a second driver circuit 84 to the Q̄ output. Thus, at any given time one of the solenoid drivers will be energized while the other driver is de-energized. The rate at which the flip-flop toggles or changes state is controlled by an integrated circuit timer 86 as, for example, the commercially available type 555 timer. An inverter gate 88 is utilized to invert and buffer the logic signal from the timer to the flip-flop. The pulse frequency produced by the timer 86 is controlled by a variable resistor 90 and capacitor 92 in a manner well known by those skilled in the art. As indicated by the pulse diagrams in FIG. 6, when the Q output of flip-flop 80 is high, solenoid driver 82 is enabled energizing valves 52 and 58. Similarly, when the Q̄ output is high, solenoid driver 84 energizes valves 54 and 56 while driver 82 is de-energized. Of course, it is possible to operate the timer in a one shot or single step mode, if desired. The pulses from the timer can be in the range of 2 to 60 pps, although preferably a rate of 15 pps is utilized.

The following example illustrates the use of the present invention with a sensor system for analyzing carbohydrates.

EXAMPLE—Carbohydrate Analyzer

Aqueous solutions containing soluble or insoluble carbohydrates (reducible as well as nonreducible sugars, starches, etc.) can be readily quantitated by employing the previously described flow injection analyzer in conjunction with a nickel oxide sensor of the type disclosed in U.S. Pat. No. 4,127,448.

The carbohydrate analyzer consists of a nickel oxide flow through electrode similar in design to the one described in U.S. Patent Application Ser. No. 898,516 filed Apr. 20, 1978. The nickel oxide sensor is connected to a heating coil as shown in FIGS. 1 through 4. The background electrolyte consists of an alkaline solution (0.01 to 4.0 moles/lt of LiOH, NaOH or KOH) containing small amounts (less than $1 \times 10^{-2}$ moles/lt) of nickel sulfate or other nickel salts. The background electrolyte is pumped through the sensor and the dual channel solution handling and sample injection system at a rate ranging from 0.10 ml/min to 50 ml/min.

Typically, the background solution consists of 0.20 moles/lt NaOH containing 0.10 moles/lt of nickel sulfate and is pumped through the flow injection analysis and sensor at a rate of 4.0 ml/min. The aqueous sample containing the carbohydrate is typically pumped at a rate of 4.0 ml/min and is injected (50 ul sample volume) into the alkaline background electrolyte stream by means of the dual channel solution handling and sample injection device. The typical sampling rate is 240 samples per hour. While the sample plug is flushed out off the sample loop, sufficient mixing occurs as to adjust the pH of the sample plug close to that of the background electrolyte. The diluted, pH adjusted sample plug is carried by the background electrolyte stream through the nickel oxide flow through electrode. The nickel oxide sensor catalytically oxidizes a representative portion of the carbohydrates in accordance with the methods and principles outlined in the patent literature as, for example, U.S. Pat. No. 4,127,448 and U.S. Patent Application Ser. No. 898,516.

The carbohydrate analyzer described above was calibrated by means of aqueous glucose standards ranging from $1 \times 10^{-5}$ moles/lt of glucose. The calibration plots (peak height vs. glucose concentrations and peak area vs. glucose concentrations) were linear over this concentration range. For ten repetitive measurements with a $1 \times 10^4$ moles/lt glucose solution, a 1.5% coefficient of variation was obtained. For thirty solutions containing unknown amounts of glucose a correlation coefficient of 0.9975 was found when the results obtained by the carbohydrate analyzer were compared with those obtained by the standard hexokinase method.

The carbohydrate analyzer is also very useful in the determination of insoluble, suspended carbohydrates (e.g. starches, etc.). Diluted suspensions of insoluble carbohydrates ranging from 1 to 2000 mg/lt have been analyzed. However, typically, diluted suspensions of carbohydrates in the range of 50–500 mg/lt are most optimal for analysis. A two percent coefficient of variation was obtained for ten repetitive measurements of an aqueous suspension (100 mg/lt) of starch. In this application of the carbohydrate analyzer the background electrolyte as well as the method and principle of analysis are identical to those outlined for the determination of glucose.

Furthermore, the carbohydate analyzer can be successfully employed in the determination of other polyhydroxy compounds such as triols and diols. For example, linear calibration plots (peak height or peak area vs. concentration) were obtained for standard glycerol solutions in the $1 \times 10^{-5}$ moles/lt to $1 \times 10^{-3}$ moles/lt concentration range. Ten repetitive measurements of aqueous glycerol standard ($1 \times 10^{-4}$ moles/lt) gave a coefficient of variation of 1.5 percent. In this application, the background electrolyte as well as the method and principle of analysis are identical to those outlined for the determination of glucose.

While I have shown and described embodiments of this invention in some detail, it will be understood that this description and illustrations are offered merely by way of example, and that the invention is to be limited in scope only by the appended claims.

I claim:

1. A solution handling apparatus for use in flow injection analysis and liquid chromatography comprising:
   (a) means for supplying background electrolyte,
   (b) means for supplying solutions for analysis,
   (c) first and second fluid carrying channels,
   (d) first valve means having first and second states for simultaneously injecting said solutions in an amount to fill one of said channels and electrolyte in an amount to fill the other of said channels in said first state and vice versa in said second state,
   (e) second valve means having first and second states for simultaneously receiving and distributing the solution from said one filled channel to one location and electrolyte from said other filled channel to a second location in said first state and vice versa in said second state,
   (f) means for simultaneous switching said first and second valve means between the first and second states in a manner described in (d) and (e) above.

2. The solution handling apparatus according to claim 1 wherein said first and second valve means are four-way solenoid operated valves.

3. The solution handling apparatus according to claim 2 wherein said four-way valves include two inlets operatively arranged to communicate with two outlets; in said first state a first inlet is connected to a first outlet, in said second state and said first inlet is connected to a second outlet, the reverse being true for said second inlet.

4. The solution handling apparatus according to claim 3 wherein said electrolyte supplying means is connected to one of said inlets of said first valve means, said solution supplying means is connected to the other of said inlets of said first valve means.

5. The solution handling apparatus according to claim 3 wherein the outlets of said second valve means are alternately connected to a means for analyzing the solutions injected into said channels, the outlet so connected being a function of the state of said second valve means.

6. The solution handling apparatus according to claim 1 wherein said switching means includes:
   (a) a pair of solenoids, one for each of said valve means for causing said valve means to switch between said first and second states,
   (b) a timer circuit,
   (c) logic means responsive to said timer circuit for operating the solenoids in alternating fashion whereby one solenoid is energized while the other is not and vice versa.

7. The solution handling apparatus according to claim 6 wherein said logic means includes a flip-flop circuit, the outputs of which drive said solenoids.

8. The solution handling apparatus according to claim 2 wherein each of said four-way valves is formed by the interconnection of two three-way valves.

9. The apparatus as claimed in claim 1 in which more than one solution handling apparatus is arranged in series.

10. The apparatus as claimed in claim 1 in which more than one solution handling apparatus is arranged in parallel.

* * * * *